(12) United States Patent
McDougald et al.

(10) Patent No.: US 7,879,342 B2
(45) Date of Patent: Feb. 1, 2011

(54) VACCINE ADJUVANT AND MAKING AND USING THE SAME

(75) Inventors: Larry R. McDougald, Watkinsville, GA (US); Alberta Lorraine Fuller, Athens, GA (US)

(73) Assignee: Univ. of Georgia Research Foundation, Inc., Athens, GA (US)

( * ) Notice: Subject to any disclaimer, the term of this patent is extended or adjusted under 35 U.S.C. 154(b) by 441 days.

(21) Appl. No.: 11/079,559

(22) Filed: Mar. 14, 2005

(65) Prior Publication Data

US 2005/0202041 A1 Sep. 15, 2005

Related U.S. Application Data

(60) Provisional application No. 60/552,636, filed on Mar. 12, 2004.

(51) Int. Cl.
| | |
|---|---|
| A61K 39/00 | (2006.01) |
| A61K 39/38 | (2006.01) |
| A61K 39/002 | (2006.01) |
| A61K 39/012 | (2006.01) |
| A61K 45/00 | (2006.01) |
| A61K 47/00 | (2006.01) |
| A61K 36/00 | (2006.01) |

(52) U.S. Cl. .............. 424/265.1; 424/184.1; 424/271.1; 424/278.1; 424/725; 424/776

(58) Field of Classification Search ........................ None
See application file for complete search history.

(56) References Cited

U.S. PATENT DOCUMENTS

| | | | | |
|---|---|---|---|---|
| 6,019,985 | A * | 2/2000 | Brown et al. ............. | 424/265.1 |
| 6,908,620 | B2 * | 6/2005 | McDougald et al. ..... | 424/267.1 |
| 6,998,127 | B2 * | 2/2006 | McDougald et al. ..... | 424/267.1 |
| 7,354,593 | B2 * | 4/2008 | McDougald et al. ..... | 424/267.1 |
| 2005/0202041 | A1 * | 9/2005 | McDougald et al. ..... | 424/202.1 |

FOREIGN PATENT DOCUMENTS

| | | | |
|---|---|---|---|
| EP | 1742656 A2 * | 1/2007 | |
| WO | WO 99/43348 A1 * | 9/1999 | |
| WO | WO 2005/089262 A2 * | 9/2005 | |

OTHER PUBLICATIONS

Allen et al, Clinical Microbiology Reviews, Jan. 2002, 15/1:58-65.*
Adel-Patient et al, Int. Arch. Allergy Immunol., 2007, 143:10-20.*
Takano et al, Biol. Pharm. Bull., 2007, 30/5:922-927.*
Wang et al, Poultry Science, Nov. 2008, 87/11:2273-2280.*
West, J.W. et al,: "Peanut Skins as a Feed Ingredient for Lactating Dairy Cows"—*Journal of Dairy Science*, 1993, vol. 76, pp. 590-599.
McBrayer, S.C. et al.: "Evaluation of Peanut Skins (TESTA) as a Feed Ingredient for Growing-Finishing Cattle"—*Journal of Animal Science*. 1983, vol. 56, pp. 173-183.
Hale, O.M. et al.: "Value of Peanut Skins (TESTA) as a Feed Ingredient for Growing-Finishing Swine"—*Journal of Animal Science*, 1981, vol. 53. pp. 1006-1010.
Utley, P.R. et al.: "Substitution of Peanut Skins for Soybean Hulls in Steer Finishing Diets Containing Recommended and Elevated Crude Protein Levels"—*Journal of Animal Science*, 1993, vol. 71, pp. 33-37.
Atuahene, C.C. et al.: "Value of Peanut Skins as a Dietary Ingredient for Broiler Chickens"—1989, *British Poultry Science*, vol. 30, No. 2, pp. 289-29388.
Lou, H. et al.: "A-type Proanthocyanidins from Peanut Skins"—*Phytochemistry: The International Journal of Plant Biochemistry and Molecular Biology*. Pergamon, 1999, vol. 51, pp. 297-308.
Karchesy, J.J. et al.: "Condensed Tannins: ($4\beta \rightarrow 8; 2\beta \rightarrow O \rightarrow 7$)-Linked Procyanidins in Arachis hypogea L"—*Journal of Agricultural and Food Chemistry*, Nov./Dec. 1986, vol. 34, No. 6, pp. 966-970.
Nepote, V. et al.: "Extraction of Antioxidant Components from Peanut Skins"—*Grasas y Aceites*, 2002, vol. 53, pp. 391-395.
Bermudez, A.J. et al.: "Disease Prevention and Diagnosis"—*Diseases of Poultry*, 11$^{th}$ Ed., 2003, pp. 17-54.
Ricks, C.A., et al.: "In Ovo Vaccination Technology" in: *Advances in Veterinary Medicine: Veterinary Vaccines and Diagnostics*, Ed. R.D. Schultz, Academis Press, 1999, vol. 41, pp. 495-515.
Schijns, V.: "Immunological Concepts of Vaccine Adjuvant Activity"—*Current Opinion in Immunology*. Aug. 2000, vol. 12. No. 4, pp. 456-463.
Singh, M. et al. "Advances in Vaccine Adjuvants"—*Nature Biotechnology*, Nov. 1999, vol. 17, pp. 1075-1081.
McDougald, L.R.: "Coccidiosis"—*Diseases of Poultry*, 11$^{th}$ Ed.,Iowa State Press, 2003, pp. 974-990.
Chapman, H.D. et al: "Sustainable Coccidiosis Control in Poultry Production: The Role of Live Vaccines"—*Int'l Journal for Parasitology*, 2002, vol. 32 pp. 617-629.
Williams, R.B.: "Anticoccidial Vaccines for Broiler Chickens: Pathways to Success" *Avian Pathology*, 2002, vol. 31, No. 4, pp. 317-353.
Long, P.L et al.: "Eimeria of American Chickens: Characteristics of Six Attenuated Strains Produced by Selection for Precocious Development"—*Avian Pathology*, 1988, vol. 17, pp. 305-314.
Lillehoj, H.S. et al.: "Adjuvanticity of Dimenthyl Dioctadecyl Ammoniuym Bromide, Complete Freund's Adjuvant and Corynebacterium Parvum with Respect to Host Immune Response to Coccidial Antigens"—*Avian Diseases*, 1993, vol. 37, pp. 731-740.
Lowenthal, J.W. et al.: "Cytokine Therapy: A Natural Alternative for Disease Control"—1999, *Veterinary Immunology and Immunopathology*, vol. 72. pp. 183-188.

(Continued)

Primary Examiner—N. M Minnifield
(74) Attorney, Agent, or Firm—Judy Jarecki-Black; Ruoying Chen; Merial Limited

(57) ABSTRACT

The present invention relates to a novel adjuvant and/or immunomodulator isolated from peanut skin extract, which may be useful in the preparation of immunogenic compositions and vaccines. The present invention also provides for a method of stimulating acquisition of protective immunity by administering peanut skin extract prior to vaccination.

7 Claims, No Drawings

OTHER PUBLICATIONS

Gore, A.B. et al.: "Enhancement of Humoral and Cellular Immunity by Vitamin E After Embryonic Exposure"—*Poultry Science*, May 1997, vol. 76, No. 5, pp. 984-991.

Allen, P.C.: "Effects of Combined Treatement with Recombinant Bovine Somatotropin and Immunization with Live Oocysts on Performance of Broiler Chicks Raised in Coccidia-Seeded Floor Pens"—*Poultry Science*, Oct. 1997, vol. 76, No. 10, pp. 1349-1354.

Fine Am: "Oligomeric Proanthocyanidin Complexes: History, Structure, and Phytopharmaceutical Applications Alternative Medicine Review, Thorne Research Inc Sandpoint" US, vol. 5, No. 2, 2000, pp. 144-151.

Lie-Chwen Lin et al: "Immunomodulatory Proanthocyanidins From Ecdysanthera Utilis" Journal of Natural Products, XX, XX, vol. 65, No. 4, Mar. 14, 2002, pp. 505-508.

Edelman, "An Update on Vaccine Adjuvants in Clinical Trial," Aids Research and Human Retroviruses 8(8):1409-1411 (1992).

McElrath, "Selection of potent immunological adjuvants for vaccine construction," seminars in Cancer Biology 6:375-385 (1995).

Aucouturier et al., "Adjuvants designed for veterinary and human vaccines," Vaccine 19:2666-2672 (2001).

East et al., "Adjuvants for New Veterinary Vaccines," Chapter I in Progress in Vaccinology, vol. 4 Veterinary Vaccines, Springer Verlag, NY 1993, pp. 1-28.

Altman et al., "Immunomodifiers in Vaccines," Advances in Veterinary Science and Comparative Medicine 33:301-343 (1989).

Wiilson et al., "Tissue Reaction and Immunity in Swine Immunized with Actinobacillus pleuropneumoniae Vaccines," Can J Vet Res 59:299-305 (1995).

* cited by examiner

VACCINE ADJUVANT AND MAKING AND USING THE SAME

INCORPORATION BY REFERENCE

This application claims priority to U.S. Provisional Application Ser. No. 60/552,636 entitled: "Novel Vaccine Adjuvant And Making And Using The Same", filed Mar. 12, 2004, the disclosure of which is incorporated by reference in its entirety.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to a novel adjuvant and/or immunomodulator isolated from peanut skin extract and a method of stimulating acquisition of protective immunity.

BACKGROUND OF THE INVENTION

The nut of the peanut (*Arachis hypogaea*) is covered in a red-pigmented testa. This material is removed in processing of peanuts for retail markets and for further processing. High quality peanut skins are available in large quantities from processing plants. Generally, this material is a waste by-product, although it is useful as a feed ingredient for livestock or poultry (see, e.g., West et al., 1993, J. Dairy Sci. 76:590-599; McBrayer et al., 1983, J. Anim. Sci. 56:173-183; Hale & McCormick, 1981, J. Anim. Sci. 53:1006-1010; Utley et al., 1993, J. Anim. Sci. 71:33-37; Atuahene et al., 1989, Brit. Poultry Sci. 30:289-293). Recent work identified peanut skins as a source for proanthocyanidins (see, e.g., Lou et al., 1999, Phytochem. 51:297-308), a group of chemicals known as the active properties in grape seed extract, marine pine bark, and other plants, which are widely touted as nutriceuticals for prevention of heart disease and other applications. Apparently, the potential value of peanut skins for medicinal or biological uses been studied only as regards treatment of chronic hemorrhage and bronchitis in Chinese herbal medicine (see, e.g., Jiangsu Xin Medical College, 1977, In: Dictionary of Chinese Materia Medics. Pub, by Shanghai Science and Technology Publisher, Shanghai China P. 2648), their high tannin content (see, e.g., Karchesy & Hemingway, 1986, J. Agr Food Chem 34: 966-970), antioxidant activity (see, e.g., Nepote et al., 2002, Grasas y Aceites, 53:391-395) and for inhibition of hyaluronidase (see, e.g., Lou, et al., 1999, Phytochem. 51:297-308). If components of peanut skins could be shown to impart useful veterinary or medical effects, the value of peanut skins could be significantly enhanced.

Broiler chicks are vaccinated at the hatchery for protection against a variety of diseases, including infectious bronchitis, Newcastle disease, Marek's disease, infectious bursal disease, coccidiosis, and other common viral diseases. Vaccination is commonly given by aerosol, injection, or by injection in ovo (see, e.g., Bermudez & Stewart-Brown, 2003, Disease prevention and diagnosis. In Diseases of Poultry, 11th edition. Ed. by Y. M. Saif, H. J. Dames, J. R. Glisson, A. M. Fadly, L. R McDougald, and D. E. Swayne. Iowa State Press, Ames Iowa, pp. 17-54; Ricks, et al. 1999, 1999, In ovo vaccination technology. Adv. Vet. Med. 41:495-515. Academic Press, San Diego Calif.). Protection against disease after vaccination is generally sufficient, but in many cases is sub-optimal due to interference with the immune system from other viruses, inadequate immunogenicity of the vaccine strains, and even pathogenicity of the vaccine strains (see, e.g., Bermudez & Stewart-Brown, 2003, Disease prevention and diagnosis. In Diseases of Poultry, 11th edition. Ed. by Y. M. Saif, H. J. Dames, J. R. Glisson, A. M. Fadly, L. R McDougald, and D. E. Swayne. Iowa State Press, Ames Iowa, pp. 17-54). Poor immune response may also be a result of bird genetics, for example, birds that are particularly poor T-cell responders. Adjuvants are not commonly used in broilers because of the possibility of adverse effects on production parameters, and damage to meat. Poor immunity against respiratory viruses leads to an increase in secondary infections and increased use of antibiotics for treatment. Previous work has identified substances, called immuno-modulators, that enhance the response of the host to specific antigens. Administration of these substances along with a vaccine or natural infection tends to cause the animal to develop a stronger immune response and more quickly, with less antigen (Schijns, 2000, Current Opin. Immunol. 12:456-463; Singh & Hagen, 1999, Natur. Biotechnol. 17:1075-1081). Coccidiosis and other diseases relying on stimulation of the cellular immune system might be better controlled if immune modulators were used in concert with the vaccine.

Coccidiosis in poultry is an excellent model for study of the use of immunomodulators in concert with live vaccines. Coccidiosis is a serious intestinal disease caused by protozoa of the genus *Eimeria*. In the US alone, coccidiosis costs the poultry industry hundreds of millions of dollars annually, including $ 100,000,000 spent on control measures (see, e.g., McDougald, 2003, Coccidiosis. In Diseases of Poultry, 11th edition, ed by Y. M. Saif, H. J. Barnes, J. R. Glisson, A. M. Fadly, L. R McDougald, and D. E. Swayne. Iowa State Press, Ames Iowa, pp. 974-990). Producers have traditionally controlled coccidiosis by extensive use of anticoccidial compounds as feed additives, used for prevention, but this approach is limited by emergence of drug resistance in field strains of coccidia (see, e.g., Chapman, et al. 2002, Int. J. Parasitol. 32:617-629) and by public outcry over perceived misuse of drugs in food animals. Producers are now turning to vaccination for control of coccidiosis (see, e.g., Williams, 2003, Avian Path. 31:317-353), as natural infections with coccidia in chickens tends to produce a strong, lasting protective response (see, e.g., Rose, 1987, Current Opin. Immunol. 12:456-463).

Coccidiosis and other diseases stimulate the cellular immune system in a complex manner, apparently mediated through CD4 lymphocytes, with little contribution by the B-cell lymphocytes (see, e.g., Lillehoj, 1998, Avian Dis. 37:731-740). The extent of protective immunity depends on several critical factors; the magnitude of the initial exposure, the species of *Eimeria*, and the bird's innate ability to mount T-cell responses. Under field conditions, the bird may be affected by viruses or other conditions which may induce immunodeficiency. Coccidiosis is mainly a disease of young birds, emphasizing the importance of early protection and rapid action of vaccines. In the vaccination of broilers, a vaccine should not adversely affect economic parameters of weight, feed conversion, skin pigmentation, or other carcass qualities. Broilers are generally grown for only a short time, being marketed at 5-8 weeks of age, giving the vaccine a short period in which to act. Some vaccines are known to depress growth and feed efficiency during the exposure period, leaving the bird little time to recover in the rapid growth stage. For this reason, milder (attenuated) strains of coccidia are being developed for use in vaccines (see, e.g., Long & Johnson, 1988, Avian Path. 17:305-314), but these have the disadvantage of being less immunogenic. Despite the possible disadvantages, pressures of modern consumer interests favors a move from chemoprevention to biological (vaccination) control of coccidiosis (see, e.g., Chapman et al., 2002, Int. J. Parasitol. 32:617-629).

Substances previously identified to stimulate the immune system for coccidiosis vaccine include *Corynebacterum parvum*, dimethyl dioctadecyl ammonium bromide, and complete Freund's adjuvant (see, e.g., Lillehoj et al, 1993, Avian Dis. 37:731-740), recombinant interferon gamma (Lowenthal et al., 1999, Vet. Immunol. Hnmunopathol. 72:183-188); vitamin E (see, e.g., Gore & Quereshi, 1997, Poultry Sci. 76:984-991) and recombinant bovine somatotrophin (see, e.g., Allen & Danforth, 1997, Poult. Sci. 76:1349-1354). These materials, while enhancing immunity to various degrees, have the disadvantage of negative effects on economic parameters.

There exists a need for a product which can be used concurrently with conventionally applied vaccines and hatchery practices, which improves the performance of vaccines without damaging hatchability or performance parameters of broiler chickens.

Citation or identification of any document in this application is not an admission that such document is available as prior art to the present invention.

SUMMARY OF THE INVENTION

The invention is based, in part, on Applicants' finding that peanut skin extract (PSE) provides significant improvements in response of chicks to vaccination (immunostimulation) if extracts are injected in ovo. Applicants demonstrated that easily extractible PSE have a strong immunostimulatory effect on the protective effects of live coccidiosis vaccines, without adverse effects on production parameters.

The present invention encompasses an immunogenic or vaccine composition which may comprise a vaccine and an adjuvant, which may comprise a peanut skin extract. In an advantageous embodiment, the composition may further comprise a pharmaceutically effective carrier. In a particularly advantageous embodiment, the vaccine is a coccidiosis vaccine. Advantageously, the coccidiosis vaccine may comprise one of more strains of *E. acervulina, E. maxima, E. mitis* or *E. tenella*. In another embodiment, the vaccine may comprise a vaccine against infectious bronchitis, infectious bursal disease, laryngotracheitis, Marek's disease or Newcastle disease, advantageously infectious bronchitis or Newcastle disease.

The present invention also encompasses an immunogenic or vaccine composition which may comprise a vaccine and an adjuvant comprising one or more proanthocyanadins, wherein the one or more proanthocyanadins is advantageously isolated from peanut skin extract. In an advantageous embodiment, the composition may further comprise a pharmaceutically effective carrier. In an advantageous embodiment, the proanthocyanadin is selected from the group consisting of epicatechin-(2β→O→7, 4β→6)-[epicatechin-(4β→8)]-catechin, epicatechin-(2β→O→7, 4β→8) epicatechin-(4β→8)-catechin-(4α→8)-epicatechin, procyanidin B2, procyanadin B3 and procyanadin B4. In a particularly advantageous embodiment, the vaccine is a coccidiosis vaccine. Advantageously, the coccidiosis vaccine may comprise one of more strains of *E. acervulina, E. maxima, E. mitis* or *E. tenella*. In another embodiment, the vaccine may comprise a vaccine against infectious bronchitis, infectious bursal disease, laryngotracheitis, Marek's disease or Newcastle disease, advantageously infectious bronchitis or Newcastle disease.

In an advantageous embodiment of the invention, any one of the vaccines described above is a live vaccine.

The invention provides for methods for eliciting an immune response which may comprise administering an effective amount of any one of the immunogenic or vaccine compositions of the present invention to induce the response in a chicken. The invention also provides for methods for inducing an immunological or protective response which may comprise administering an effective amount of any one of the immunogenic or vaccine compositions of the present invention to induce the response in a chicken. The immunogenic or vaccine composition may be administered to a chicken by oral gavage, in a spray cabinet, as a dietary supplement or as a subcutaneous injection, advantageously in neck skin. The chicken may be newly hatched or one day old when the composition is administered.

The invention also encompasses method of stimulating acquisition of protective immunity which may comprise administering an effective amount of peanut skin extract and/or one or more proanthocyanadins prior to vaccination with an effective amount of a vaccine, advantageously a live vaccine, to stimulate acquisition of protective immunity in a chicken. In one embodiment, the amount of peanut skin extract is about 60 micrograms to about 1000 micrograms, advantageously about 250 micrograms. In an advantageous embodiment, the proanthocyanadin is selected from the group consisting of epicatechin-(2β→O→7, 4β→6)-[epicatechin-(4β→8)]-catechin, epicatechin-(2β→O→7, 4β→8) epicatechin-(4β→8)-catechin-(4α→8)-epicatechin, procyanidin B2, procyanadin B3 and procyanadin B4. In one embodiment, the chicken is a chicken embryo, advantageously an 18 day chicken embryo when the peanut skin extract and/or one or more proanthocyanadins is administered, advantageously by injection.

The immunogenic or vaccine composition may be administered to a chicken by oral gavage, in a spray cabinet, as a dietary supplement or as a subcutaneous injection, advantageously in neck skin. The chicken may be newly hatched or one day old when the composition is administered.

The invention also provides for kits encompassing the compositions and/or methods described herein.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DETAILED DESCRIPTION

Poultry meat is the largest source of meat in the American diet. More than $10 \times 10^9$ broiler chickens are hatched and reared to market weight annually in America, and approximately 3 times this number outside the USA. The problems with disease control are increasing because of the emergence of more virulent forms of old diseases, and of new diseases, as well as the shortcomings of the immune system of birds bred for rapid growth. The value of a product to improve performance of vaccines could be equivalent to the cost of a vaccine. There is no comparable product to use in gauging the value of the market for immunostimulants. However, given that the proposed product could be produced and sold with a suitable net profit margin, and at a price compatible with the economics of the broiler industry, one could estimate a market in the USA of approximately $100,000,000. Similar possibilities are likely for well developed international markets in Europe and South America. Given the ease of extraction of PSE, its apparent stability to heat, and the readily available raw material, the product could be produced within economically acceptable parameters, while improving the value of the raw material to the producer.

The present invention encompasses an immunogenic or vaccine composition which may comprise a vaccine and an adjuvant which may comprise a peanut skin extract, which may further comprise a pharmaceutically effective carrier.

In a particularly advantageous embodiment, the vaccine is a coccidiosis vaccine. Advantageously, the coccidiosis vaccine may comprise one of more strains of *E. acervulina, E. maxima, E. mitis* or *E. tenella*. In consideration of the prevalence and pathogenicity of various *Eimeria* species, a successful attenuated coccidiosis vaccine should contain the least number of *Eimeria* strains sufficient to elicit an immune response or induce an immunological or protective response that is non-pathogenic to the recipient of the vaccine. The addition of other *Eimeria* strains, such as *E. brunetti, E. necatrix* and *E. praecox* may be disadvantageous with respect to efficacy, cross-infection or pathogenicity of the vaccine. Since *E. brunetti, E. necatrix* and *E. praecox* are not necessary for the efficacy of the coccidiosis vaccine disclosed herein, it would be advantageous to exclude these strains from the vaccine of the present invention.

Stock cultures of the *Eimeria* strains for the seed cultures include, but are not limited to, the following. The parent of the *Eimeria acervulina*, obtained from T. K. Jeffers at Hess and Clark Laboratories in 1969, was thought to have been isolated by Dr. M. M. Farr at USDA, Beltsville, Md., which was derived from a single oocyst. The *Eimeria maxima* culture was derived from an interbred mixture of 10 purified isolates obtained from Georgia, Delaware, Maryland, Virginia and Texas. The parent of the *Eimeria mitis* culture was isolated from Gainesville, Ga. in July 1978 and was purified by single oocyst isolation. The parent of the *Eimeria tenella* culture was obtained from a culture maintained at Pennsylvania State University by Dr. Patten since the early 1960's, and was acquired by the University of Georgia in 1982. Other precocious *Eimeria* strains include LS 100 precocious *E. Acervulina* isolate 809-13, and LS precocious *E. mitis*, obtained from Merck Research Laboratories, which were obtained from Dr. Peter Long. Alternatively, attenuated precocious *Eimeria* lines that have been deposited as sporocysts at the European Collection of Animal Cell Cultures ("ECACC") as patent deposits (see, e.g., U.S. Pat. No. 5,055,292, the disclosure of which is incorporated by reference in its entirety) are useful stock cultures to generate the *Eimeria* seed cultures described herein. Specifically, deposits of *E. acervulina* (deposit no. ECACC 86072203), *E. maxima* (deposit nos. ECACC 86112011 and 86112012), *E. mitis* (deposit no. ECACC 86072206) and *E. tenella* (deposit no. ECACC 86072201) as described in U.S. Pat. No. 5,055,292 are useful stock cultures for the seed cultures of the present invention.

Advantageously, the microorganisms are attenuated by their selection for precocious development as described above. In another advantageous embodiment, the culture is pathogen-free. The stock cultures described above are advantageously maintained in the liquid or vapor phase of liquid nitrogen. Such methods are known to one of skill in the art.

In an advantageous embodiment, the chickens are two to eight weeks old. Sporulated oocysts are passed successively, without limitations to the passage, in chickens until the number of oocysts are sufficient to be used as seed for production. Advantageously, the cultures should not be held for longer than 12 months in order to maintain viability/infectivity.

In an advantageous embodiment, dedicated facilities are maintained for each *Eimeria* species. Advantageously, a sufficient volume of sporulated oocysts (seed) is mixed with feed or alternatively, is administered orally to provide each chicken with a minimum dose. In an advantageous embodiment, about 5000 to about 15,000 oocytes are seeded per chicken to generate the seed culture.

The sporulated oocysts from the seed culture are isolated from the bird feces, advantageously by centrifugation. In an advantageous embodiment, the harvest is as follows. Droppings are homogenized at an approximate ratio of 10% (w/v) in water. Large particles are removed by passing homogenate through screens. Solids are separated by either centrifugation, screening or by holding at 5±3° C. up to 24 hours. If solids are separated by holding at 5±3° C., they are further concentrated by centrifugation. The supernatant is discarded, and the solids are resuspended in a saturated NaCl (80% w/v) solution in water. The resulting solution is centrifuged. The oocysts are collected (removed) from the top of the liquid, and resuspended in water. Optionally, the remaining liquid is diluted to 20-40% NaCl with water and centrifuged. The pellet is then resuspended in a saturated NaCl solution and re-centrifuged, until no additional oocysts are recovered. The oocysts are washed no more than twice. The oocysts are washed free of salt by repeated, resuspension centrifugation cycles-followed by resuspension in a 0.5% solution of sodium hypochlorite for 10 to 15 minutes. The oocysts are then washed free of the sodium hypochlorite solution by repeated (3×) centrifugation and resuspension steps. The final resuspension is made in a 2.5% aqueous solution of potassium dichromate ($K_2CrO_7$). The oocysts were then transferred to sporulation vessels. Sporulation is facilitated by sparging the suspensions with air for a period not to exceed 72 hours at 27±3° C. Following sporulation the oocysts are held at 5±3° C. until the final product is produced.

In another embodiment, oocysts to be used in accord with the present vaccination method can be prepared by any of several methods known to those skilled in the art. Such methods include those described in J. F. Ryley at al., Parasitology 73:311-326, 1976, P. L. Long et al., Folia Veterinaria Latina VI#3, 201-217, 1976, and U.S. Pat. No. 6,627,205, the disclosures of which are incorporated by reference in their entireties. According to one method, commercial broiler chickens, approximately 2 weeks old, are infected with the *Eimeria* species of interest by oral gavage of an appropriate dose of sporulated oocysts. Well known procedures for collection and purification of oocysts from infected birds are then followed. For most species of *Eimeria*, feces are collected from infected birds 5-7 days post-infection, blended and filtered to remove debris, then centrifuged at a speed sufficient to pellet the remaining fecal material. The pellet is resuspended in a saturated salt solution, in which the oocysts float and most of the contaminating debris can be removed by centrifugation. The oocyst suspension is then diluted to lower the salt concentration. The oocysts are washed repeatedly to remove the salt and resuspended in potassium dichromate solution (2.5% w/v). The oocyst suspension is incubated at 29 C with shaking (e.g., 140 rpm) for approximately 72 hours to induce sporulation of the oocysts. Alternatively, the oocysts can be treated with sodium hypochlorite and then sporulated. The number of sporulated oocysts/ml is determined by direct count using a hemocytometer or McMaster slide, and the culture is stored under refrigeration until needed.

To prepare sporocysts, the potassium dichromate is removed from the oocyst suspension described above by repeated washing of the oocysts, which involves collection of oocysts by centrifugation and resuspending in deionized or distilled water. When the dichromate has been removed as judged by the lack of yellowish-orange coloration, the oocyst suspension is mixed with an equal volume of sodium hypochlorite (bleach) and incubated at room temperature for 15 minutes. The bleach is then removed by repeated washings, and the oocysts are resuspended in physiological saline or deionized water. Oocysts can be broken to release sporocysts using a variety of known techniques. For example, oocysts can be broken to release sporocysts by mixing the oocysts with glass beads of 1-4 mm diameter and shaking by hand, vortex mixer, or shaking incubator, or using a hand-held homogenizer. Unbroken oocysts and oocysts walls can be separated from the released sporocysts by differential centrifugation in 50% PERCOLL, a colloidal suspension of polyvinyl pyrrolidone coated silica particles (sold by Pharmacia Biotech) or 1 M sucrose as described in Dulski et al., Avian Diseases, 32: 235-239, 1988. The sporocysts can be used in the present vaccination method either mixed with or separated from the unbroken oocysts and oocysts walls. Advantageously, the dose of sporocysts is separated from the oocysts and oocysts walls.

In an advantageous embodiment, the specifications for an acceptable harvest of the seed culture are as follows. First, the ratio of sporulated oocysts to total oocysts was determined. Only harvests meeting or exceeding >40% sporulation are considered acceptable. Second, the size, shape and appearance of each oocyst harvest must be characteristic of the species intended to be produced. For example, parameters to be considered in characterizing the *Eimeria* species include, but are not limited to, DNA-based technologies, DNA buoyant density, enzyme variation, host and site specificity, immunological specificity, pathogenicity, pre-patent period and sporulation time (see, e.g., Long & Joyner, J Protozool. 1984 November; 31(4): 535-41 and Shirley, Acta Vet Hung. 1997; 45(3): 331-47, the disclosures of which are incorporated by reference).

The isolated sporulated oocysts from the seed cultures described herein may be useful for the vaccination of a bird. In an advantageous embodiment, the dosage of *E. tenella* oocysts is about 1000 oocysts per bird. In another embodiment, sporulated oocysts isolated from one or more strains of *E. acervulina, E. maxima, E. mitis* and *E. tenella* are useful for methods and compositions of the present invention. Reference is made to the attenuated coccidiosis vaccines of U.S. patent application Ser. No. 10/730,206 filed Dec. 8, 2003 and published as U.S. Patent Publication No. 20040120973 on Jun. 24, 2004 for representative mixtures of *Eimeria* strains.

Advantageously, the oocysts are suspended in a preservative consisting of a 0.01M phosphate buffered saline solution containing gentamicin. In another embodiment, the oocysts are suspended in any one of a variety of preservatives or organic acids such as, but not limited to, acetic acid, citric acid, potassium dichromate or propionic acid. For example, but not by limitation, sufficient sterile, 0.01M phosphate buffered saline containing not more than 30 mcg/ml gentamicin, is used to yield 2 ml per bottle for a 2,000 dose presentation, 5 ml per bottle for a 5,000 dose presentation and 10 ml per bottle for a 10,000 dose presentation. Advantageously, the oocysts are stored in sterile, borosilicate glass vials. For example, but not by limitation, the oocysts are aseptically filled into vaccine vials with a semi-automatic or automatic dispenser, stoppers are mechanically or manually inserted and aluminum seals are placed and crimped.

In another embodiment, oocysts are suspended in sterile distilled water containing a suspending agent, for example a polysaccharide suspending agent such as a gum, e.g. xanthan gum or gum acacia, a cellulose derivative, e.g. carboxymethyl cellulose, hydroxypropyl methyl cellulose or microcrystalline cellulose, carageenan, sodium alginate, pectin or starch; a polypeptide suspending agent such as gelatin; a synthetic polymer suspending agent such as polyacrylic acid; or a silicate suspending agent such as magnesium aluminium silicate (see, e.g., U.S. Pat. No. 5,055,292.

The present invention also provides for verifying the size, shape and appearance of each oocyst harvest are characteristic of the species intended to be produced. In yet another advantageous embodiment, the sporulated oocysts are tested for purity, extraneous pathogens, and/or deaths or severe lesions of the test animals, e.g., chickens. The characteristics of the various *Eimeria* species are fully set out by Long P. L. and Reid W. M. (1982: A Guide for the Diagnosis of Coccidiosis in Chickens; University of Georgia Research Report 404) and Joyner L. P. (1978: Identification and Diagnosis, Avian Coccidiosis, Poultry Science Symposium No. 13, British Poultry Science Ltd).

The cocciodiosis vaccines of U.S. Pat. Nos. 4,438,097; 4,639,372; 4,808,404; 5,055,292; 5,068,104; 5,387,414; 5,602,033; 5,614,195; 5,635,181; 5,637,487; 5,674,484; 5,677,438; 5,709,862; 5,780,289; 5,795,741; 5,814,320; 5,843,722; 5,846,527; 5,885,568; 5,932,225; 6,001,363 and 6,100,241, which include live and recombinant vaccines, may also be employed in the present invention. Advantageously, the coccidiosis vaccine is a live vaccine. However, attenuated coccidiosis vaccines, such as the vaccines described in U.S. patent application Ser. No. 10/730,206 filed Dec. 8, 2003 and published as U.S. Patent Publication No. 20040120973 on Jun. 24, 2004, the disclosure of which is incorporated by reference, may also be used in the present invention.

In another embodiment, the vaccine may comprise an infectious bronchitis, infectious bursal disease, laryngotracheitis, Marek's disease or Newcastle disease vaccine, advantageously an infectious bronchitis or Newcastle disease vaccine. Advantageously, the vaccine is a live vaccine. The vaccines against infectious bronchitis described in U.S. Pat. Nos. 6,733,759; 6,576,757; 6,569,435; 6,541,011; 6,299,874; 6,210,718; 6,086,892; 5,976,580; 5,884,583; 5,750,113; RE34,013; 4,867,975; 4,761,282; 4,751,079; 4,645,665; 4,505,892; RE31,830; 4,357,320; 4,235,876 and 4,053,583 are useful for the present invention. The vaccines against infectious bursal disease described in U.S. Pat. Nos. 6,764, 684; 6,733,759; 6,210,718; 6,129,920; 6,019,985; 5,976,580; 5,807,551; 5,605,827; 5,605,792; 4,824,668 and 4,530,831 are useful for the present invention. The vaccines against laryngotracheitis described in U.S. Pat. Nos. 6,592,869; 6,541,001; 5,884,583; 4,980,162 and 4,928,629 are useful for the present invention. The vaccines against Marek's disease described in U.S. Pat. Nos. 6,723,324; 6,485,940; 6,451,321; 6,406,843; 5,690,939; 5,686,287; 5,378,467; 5,283,191; 5,106,616; 4,224,413; 4,144,126 and 4,127,648 are useful for the present invention. The vaccines against Newcastle disease described in U.S. Pat. Nos. 6,713,073; 6,592,869; 6,541,001; 6,509,446; 6,406,702; 6,319,693; 6,299,874; 6,286,455;

6,238,669; 6,048,535; 6,032,612; 5,958,424; 5,932,476; 5,884,583; 5,817,320; 5,750,111; 5,750,101; 5,561,062; 5,491,073; 5,422,109; 5,250,298; 5,149,530; 5,124,148; 5,118,502; 4,877,612; 4,795,635; 4,251,509; 4,235,876 and 3,949,070 are useful for the present invention.

The invention further provides for determining bird performance as defined by feed conversion rates as a result of administering the compositions described herein. Feed conversion efficiency is defined as the as pounds of feed to produce a pound of meat. A common result is about 1.90 or 2.00. One point in feed conversion in common lingo is 0.01, which equals about 0.5% (half of a percent). If the metric system is used, the feed conversion is Kg of feed per Kg of meat, and is still proportional to the above.

The present invention relates to immunizing a chicken, advantageously a broiler chicken. However, methods of making the vaccine described herein can be extrapolated to other animals infected by *Eimeria*, in particular avians such as, but not limited to, a chicken, duck, goose, guinea fowl, peafowl, pheasant, pigeon, quail or turkey, or in a less advantageous embodiment, a rabbit.

The term of "immunogenic composition" covers herein any composition able, once it has been administered to an animal, e.g., avian, to elicit a protective immune response against the parasite or antigen or immunogen or epitope. The term of "vaccine" covers herein any composition able, once it has been administered to the animal, e.g., avian, to induce a protective immune response against the virus, or to efficaciously protect the animal against infection.

Immunogenic compositions or vaccines according to the invention can also include the pathogen or immunogen, antigen or epitope of the pathogen and at least one immunogen, antigen or epitope of another pathogen, parasite or virus, for example, the coccidiosis vaccine is combined with another avian vaccine. Such an immunogen, antigen or epitope may e.g. be of bacterial, or parasitic or viral origin or an inactivated or attenuated form of the pathogen, parasite or virus. The invention also comprehends kits to prepare these combination compositions, as well as methods for making these combination compositions and the use of the components of these combination compositions to prepare the combination compositions. Accordingly, the invention involves a kit for preparing the combination immunogenic or vaccine compositions of the invention; for instance, such a kit that comprises (a) an organism, pathogen or virus or antigen or epitope thereof (advantageously a pathogen as mentioned herein) and (b) an organism, pathogen or virus or immunogen, antigen or epitope thereof (advantageously a virus or immunogen, antigen or epitope thereof, but other pathogens as herein mentioned are also contemplated) that is different than (a), in separate containers, optionally in the same package, and optionally with instructions for admixture and/or administration.

Immunogenic compositions and/or vaccines according to the invention can include, for example, *Eimeria* culture or preparation (e.g., live, inactivated or attenuated *Eimeria*, or an immunogen or antigen or epitope thereof), and at least one immunogen, antigen or epitope of another avian pathogen (including without limitation the pathogen in inactivated or attenuated form). For avian multivalent immunogenic compositions and multivalent vaccines, the additional avian pathogen(s), as to which additional avian antigen(s) or immunogen(s) or epitope(s) thereof are included in and/or expressed by the multivalent immunogenic compositions and multivalent vaccines, are viruses, diseases, or pathogens of the Marek's disease virus (MDV) (e.g., serotypes 1 and 2, advantageously 1), Newcastle disease virus (NDV), paramyxoviruses other than Newcastle disease (PMV2 to PMV7), infectious bronchitis virus (IBV), infectious anaemia virus or chicken anemia virus (CAV), infectious laryngotracheitis virus (ILTV), infectious bursal disease virus (IBDV), encephalomyelitis virus or avian encephalomyelitis virus (AEV or avian leukosis virus ALV), virus of hemorragic enteritis of turkeys (HEV), pneumovirosis virus (TRTV), fowl plague virus (avian influenza), chicken hydropericarditis virus, avian reoviruses, coccidiosis, egg drop syndrome (EDS76), fowl pox, inclusion body hepatitis (adenovirus), lymphoproliferative disease of turkeys, reticuloendotheliosis in chickens, reticuloendotheliosis in turkeys, rotavirus enteritis, and turkey rhinotracheitis, *Clostridium* spp., *Escherichia coli, Mycoplasma gallinarum, Mycoplasma gallisepticum, Haemophilus avium, Pasteurella gallinarum, Pasteurella multocida gallicida*, and mixtures thereof. Advantageously, for MDV the immunogen is advantageously gB and/or gD, e.g., gB and gD, for NDV the immunogen is advantageously HN and/or F, e.g., HN and F; for IBDV the immunogen advantageously is VP2; for IBV the immunogen is advantageously S (more advantageously S1) and/or M and/or N, e.g., S (or S1) and M and/or N; for CAV the immunogen is advantageously VP1 and/or VP2; for ILTV the immunogen is advantageously gB and/or gD; for AEV the immunogen advantageously is env and/or gag/pro, e.g., env and gag/pro or gag/pro; for HEV the immunogen is advantageously the 100K protein and/or hexon; for TRTV the immunogen is advantageously F and/or G, and for fowl plague the immunogen is advantageously HA and/or N and/or NP, e.g., HA and N and/or NP. Thus, the invention also involves methods for making these compositions, as well as kits therefor.

An immunogenic composition or vaccine according to the invention that also comprises such an additional immunogenic component (additional immunogen, antigen or epitope) has the advantage that it induces an immune response or protection against several infections or maladies or causative agents thereof at the same time. This additional immunogenic component can be an attenuated or inactivated micro-organism, a recombinant construct or sub-units (e.g. proteins, glycoproteins, polypeptides, or epitopes). Epitope determination procedures, such as, generating overlapping peptide libraries (Hemmer et al., Immunology Today, 1998, 19 (4), 163-168), Pepscan (Geysen H. M. et al., Proc. Nat. Acad. Sci. USA, 1984, 81 (13), 3998-4002; Geysen H. M. et al., Proc. Nat. Acad. Sci. USA, 1985, 82 (1), 178-182; Van der Zee R. et al., Eur. J. Immunol., 1989, 19 (1), 43-47; Geysen H. M., Southeast Asian J. Trop. Med. Public Health, 1990, 21 (4), 523-533; Multipin Peptide Synthesis Kits de Chiron) and algorithms (De Groot A. et al., Nature Biotechnology, 1999, 17, 533-561), can be used in the practice of the invention, to determine epitopes of immunogens, antigens, polypeptides, glycoproteins and the like, without undue experimentation. From that information, one can construct nucleic acid molecules encoding such an epitope, and from that knowledge and knowledge in the art, one can construct vectors or constructs, e.g., recombinant viruses or vectors or plasmids that express immunogens, epitopes or antigens; all without undue experimentation.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description of immunization and vaccination methods, and can also be determined by the skilled artisan from this disclosure read in conjunction with the knowledge in the art, without any undue experimentation.

The present invention relates to a novel adjuvant and/or immunomodulator. The adjuvant and/or immunomodulator comprises one or more compounds, advantageously one or more proanthocyanidin(s). The proanthocyanidin(s) can be isolated from a naturally occurring source, such as a food or beverage typically consumed by an animal such as human, e.g, the proanthocyanidin can be extracted from a natural source such as tea, grapes, wine, cocoa or peanuts, and is advantageously from a peanut skin extract (reviewed in, e.g., Lesschaeve & Noble, Am J Clin Nutr. 2005 January; 81(1 Suppl):330S-335S; Yu et al., Sheng Wu Yi Xue Gong Cheng Xue Za Zhi. 2004 June; 21(3):476-81; Cos et al., Curr Med. Chem. 2004 May; 11(10):1345-59; Ferreira & Marais, Phytochemistry. 2003 September; 64(1):31-51; Marles et al., Phytochemistry. 2003 September; 64(2):367-83; Bagchi et al., Mutat Res. 2003 February-March; 523-524:87-97; Ferreira & Slade, Nat Prod Rep. 2002 October; 19(5):517-41; van Beek, J Chromatogr A. 2002 Aug. 16; 967(1):21-55; Teixeira, J Orthop Sports Phys Ther. 2002 July; 32(7):357-63; Bagchi et al., Ann N Y Acad. Sci. 2002 May; 957:260-70; Preuss et al., Ann N Y Acad. Sci. 2002 May; 957:250-9; Sen et al., Ann N Y Acad. Sci. 2002 May; 957:239-49; Howell, Crit Rev Food Sci Nutr. 2002; 42(3 Suppl):273-8; Scalbert et al., Biofactors. 2000; 13(1-4):115-20; Ferreira & Li, Nat Prod Rep. 2000 April; 17(2):193-212; Tanaka et al., Basic Life Sci. 1999; 66:761-78; Mitsunaga, Basic Life Sci. 1999; 66:555-73; Fine, Altem Med Rev. 2000 April; 5(2):144-51; Das et al., Drugs Exp Clin Res. 1999; 25(2-3):115-20; Kinghorn et al., Med Res Rev. 1998 September; 18(5):347-60 and Heilmann & Merfort, Pharm Unserer Zeit. 1998 July; 27(4):173-83). See also U.S. Pat. Nos. 6,805,883; 6,790,966; 6,777,005; 6,747,059; 6,720,432; 6,696,485; 6,670,390; 6,638,971; 6,562,863; 6,517,841; 6,479,539; 6,469,053; 6,297,273; 6,225,338; 6,156,791; 5,891,905; 5,877,206; 5,712,305 and 5,554,645. However, the compound(s) can also be synthetically prepared (see, e.g., U.S. Pat. Nos. 6,864,377; 6,849,746; 6,528,664; 6,476,241; 6,420,572; 6,207,842 and 6,156,912 and Delcour et al., 1985, J. Chem. Soc. Perkin Trans. I:669-676 and 1983, J. Chem. Soc. Perkin Trans. I: 1535-1543).

Thus, the invention comprehends an adjuvant and/or immunomodulator comprising or consisting essentially of one or more proanthocyanidin(s). Advantageously, the invention comprehends an adjuvant and/or immunomodulator comprising or consisting essentially of one or more proanthocyanidin(s) and/or an extract from a natural source such as tea, grapes, wine, cocoa or peanuts; and more advantageously a peanut skin extract, e.g., an adjuvant and/or immunomodulator comprising or consisting essentially of an extract of tea, grapes, wine cocoa or peanuts, e.g., peanut skin, comprising or consisting essentially of one or more proanthocyanidin(s); for instance an adjuvant and/or immunomodulator comprising or consisting essentially of a peanut skin extract comprising or consisting essentially of one or more proanthocyanidin(s). The invention additionally relates to a method of stimulating acquisition of protective immunity, as well as to a method of increasing or enhancing the immunogenicity of an antigen. The methods involve employing an inventive adjuvant with an antigen and administering the antigen and adjuvant, either in admixture or serially, to enhance the immunogenicity of the antigen, as well as to stimulate immunity. The antigen is advantageously a coccidiosis antigen. In an advantageous embodiment, the effective amount of peanut skin extract as an adjuvant and/or immunomodulator is about 60 micrograms to about 1000 micrograms, advantageously about 250 micrograms. The peanut skin adjuvant may be extracted from peanut skins in boiling water, as described by Lou et al. (1999, Phytochem. 51:297-308). The extract is concentrated by cryo-evaporation to dryness and reconstituted in physiological saline for injection. However, other methods for extracting the peanut skin adjuvant are contemplated for methods of the present invention.

In another embodiment, the inventive adjuvant and/or immunomodulator may additional comprise or consist essentially of vitamin E. In an advantageous embodiment, the effective amount of vitamin E as an adjuvant and/or immunomodulator is about 10 IU to about 30 IU.

The immunogenic compositions and vaccines according to the invention may comprise or consist essentially of one or more adjuvants in addition to the peanut skin extract and/or one or more proanthocyanadins described above. Additional adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., Proc. Natl. Acad. Sci., USA, 1996, 93, 2879-2883; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, (5) cytokines, (6) aluminum hydroxide or aluminum phosphate or (7) other adjuvants discussed in any document cited and incorporated by reference into the instant application, or (8) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as PLURONIC, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name CARBOPOL (BF Goodrich, Ohio, USA) are especially suitable. They are crosslinked by allyl saccharose or by allyl pentaerythritol. Among them, reference is made to CARBOPOL 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to J. Fields et al., Nature 186: 778-780, Jun. 4, 1960.

With regard to structure, the acrylic or methacrylic acid polymers and EMA are preferably formed by basic units having the following formula:

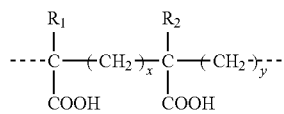

in which:
R$_1$ and R$_2$, which can be the same or different, represent H or CH$_3$
x=0 or 1, preferably x=1
y=1 or 2, with x+y=2.
For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final vaccine composition can range between 0.01 and 1.5% w/v, advantageously 0.05 to 1% w/v and preferably 0.1 to 0.4% w/v.

The cationic lipids (4) containing a quaternary ammonium salt which are advantageously but not exclusively suitable for plasmids, are preferably those having the

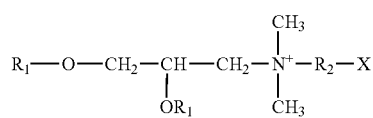

following formula:
in which R$_1$ is a saturated or unsaturated straight-chain aliphatic radical having 12 to 18 carbon atoms, R$_2$ is another aliphatic radical containing 2 or 3 carbon atoms and X is an amine or hydroxyl group.

Among these cationic lipids, preference is given to DMRIE (N-(2-hydroxyethyl)-N,N-dimethyl-2,3-bis(tetradecyloxy)-1-propane ammonium; WO96/34109), preferably associated with a neutral lipid, preferably DOPE (dioleoyl-phosphatidyl-ethanol amine; Behr J. P., 1994, Bioconjugate Chemistry, 5, 382-389), to form DMRIE-DOPE.

Advantageously, the mixture with the adjuvant is formed extemporaneously and preferably contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is preferably about 95:about 5 to about 5:about 95, more advantageously about 1:about 1, e.g., 1:1.

The DMRIE or DMRIE-DOPE adjuvant:plasmid weight ratio can be between about 50:about 1 and about 1:about 10, such as about 10:about 1 and about 1:about 5, and preferably about 1:about 1 and about 1:about 2, e.g., 1:1 and 1:2.

The cytokine or cytokines (5) can be in protein form in the immunogenic or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector therefor.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon α (IFN α), interferon β (IFN β), interferon γ, (IFN γ), interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNF α), tumor necrosis factor β(TNF β), and transforming growth factor β (TGF β). It is understood that cytokines can be co-administered and/or sequentially administered with the immunogenic or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, an avian cytokine for preparations to be administered to birds).

Another aspect of the present invention is a method of immunization or a method of vaccination using the immunogenic compositions or the vaccine compositions according to the invention, respectively. The invention provides for methods for eliciting an immune response which may comprise administering an effective amount of any one of the immunogenic or vaccine compositions of the present invention to induce the response in a chicken. The invention also provides for methods for inducing an immunological or protective response which may comprise administering an effective amount of any one of the immunogenic or vaccine compositions of the present invention to induce the response in a chicken.

The invention also encompasses method of stimulating acquisition of protective immunity which may comprise administering an effective amount of peanut skin extract and/or one or more proanthocyanadins prior to vaccination with an effective amount of a vaccine, advantageously a live vaccine, to stimulate acquisition of protective immunity in a chicken. In one embodiment, the chicken is a chicken embryo, advantageously an 18 day chicken embryo when the peanut skin extract and/or one or more proanthocyanadins is administered, advantageously by injection.

The method includes at least one administration to an animal of an efficient amount of the immunogenic composition or vaccine according to the invention. The animal may be male or female. This administration may be notably done by intramuscular (IM), intradermal (ID) or subcutaneous (SC) injection, advantageously in the neck skin, or via oral administration, wherein oral administration includes but is not limited to administration on feed or in drinking water, gels, or sprays. The immunogenic composition or the vaccine according to the invention can be administered by a syringe or a needleless apparatus (like for example AVIJET, PIGJET, or BIOJECTOR (Bioject, Oregon, USA)). In an advantageous embodiment, the administration is oral, advantageously by oral gavage.

The compositions according to the invention may also be administered to other mammals, e.g. mice or laboratory animal, for instance to generate polyclonal antibodies, or to prepare hybridomas for monoclonal antibodies.

The in ovo administration of peanut skin extract and/or the proanthocyanadin(s) as described hereinabove, involves the administration of the vaccine to the avian embryo while contained in the egg. The peanut skin extract and/or the proanthocyanadin(s) may be administered to any suitable compartment of the egg (e.g., allantois, yolk sac, amnion, air cell, or into the avian embryo itself), as would apparent to one skilled in the art. Advantageously, the vaccine is administered to the amnion. Eggs administered the peanut skin extract and/or the proanthocyanadin(s) of the present invention are fertile eggs which are advantageously in the last half, more advantageously the last quarter, of incubation. Chicken eggs are treated on about the twelfth to twentieth day of incubation, more advantageously the fifteenth to nineteenth day of incubation, and are most advantageously treated on about the eighteenth day of incubation (the eighteenth day of embryonic development). Turkey eggs are advantageously treated on about the fourteenth to twenty-sixth day of incubation, more advantageously on about the twenty-first to twenty-seventh day of incubation, most advantageously on about the twenty-fifth day of incubation. Those skilled in the art will appreciate that the present invention can be carried out at any predetermined time in ovo.

Eggs may be administered the peanut skin extract and/or the proanthocyanadin(s) by any means which transports the compound through the shell. The advantageous method of administration is, however, by injection. The substance may be placed within an extraembryonic compartment of the egg (e.g., yolk sac, amnion, allantois, air cell) or within the embryo itself. The site of injection is advantageously within the region defined by the amnion, including the amniotic fluid and the embryo itself. By the beginning of the fourth quarter of incubation, the anmion is sufficiently enlarged that penetration thereof is assured nearly all of the time when the injection is made from the center of the large end of the egg along the longitudinal axis.

The mechanism of egg injection is not critical, but it is advantageous that the method not unduly damage the tissues and organs of the embryo or the extraembryonic membranes surrounding it so that the treatment does not decrease hatch rate. A hypodermic syringe fitted with a needle of about 18 to 22 gauge is suitable for the purpose. To inject into the air cell, the needle need only be inserted into the egg by about two millimeters. A one-inch needle, when fully inserted from the center of the large end of the egg, penetrates the shell, the outer and inner shell membranes enclosing the air cell, and the anmion. Depending on the precise stage of development and position of the embryo, a needle of this length terminates either in the fluid above the chick or in the chick itself. A pilot hole may be punched or drilled through the shell prior to insertion of the needle to prevent damaging or dulling of the needle. If desired, the egg can be sealed with a substantially bacteria-impermeable sealing material such as wax or the like to prevent subsequent entry of undesirable bacteria.

It is envisioned that a high-speed automated egg injection system for avian embryos are particularly suitable for practicing the present invention. Numerous such devices are available, exemplary being those disclosed in U.S. Pat. Nos. 4,681,063, 4,903,635, 4,040,388, 4,469,047, and 4,593,646. All such devices, as adapted for practicing the present invention, comprise an injector containing the vaccine described herein, with the injector positioned to inject an egg carried by the apparatus with the vaccine. Other features of the apparatus are discussed above. In addition, if desired, a sealing apparatus operatively associated with the injection apparatus may be provided for sealing the hole in the egg after injection thereof.

The present invention also provides for the immunization of animals, advantageously avians, following the stimulating acquisition of protective immunity. Methods for administering coccidiosis vaccines are described in U.S. Pat. Nos. 4,438,097; 4,639,372; 4,808,404; 5,055,292; 5,068,104; 5,387,414; 5,602,033; 5,614,195; 5,635,181; 5,637,487; 5,674,484; 5,677,438; 5,709,862; 5,780,289; 5,795,741; 5,814,320; 5,843,722; 5,846,527; 5,885,568; 5,932,225; 6,001,363 and 6,100,241. Methods for administering infectious bronchitis vaccine are described in U.S. Pat. Nos. 6,733,759; 6,576,757; 6,569,435; 6,541,011; 6,299,874; 6,210,718; 6,086,892; 5,976,580; 5,884,583; 5,750,113; RE34,013; 4,867,975; 4,761,282; 4,751,079; 4,645,665; 4,505,892; RE31,830; 4,357,320; 4,235,876 and 4,053,583. Methods for administering infectious bursal disease vaccine are described in U.S. Pat. Nos. 6,764,684; 6,733,759; 6,210,718; 6,129,920; 6,019,985; 5,976,580; 5,807,551; 5,605,827; 5,605,792; 4,824,668 and 4,530,831. Methods for administering laryngotracheitis vaccine are described in U.S. Pat. Nos. 6,592,869; 6,541,001; 5,884,583; 4,980,162 and 4,928,629. Methods for administering Marek's disease vaccine are described in U.S. Pat. Nos. 6,723,324; 6,485,940; 6,451,321; 6,406,843; 5,690,939; 5,686,287; 5,378,467; 5,283,191; 5,106,616; 4,224,413; 4,144,126 and 4,127,648. Methods for administering Newcastle disease vaccine are described in U.S. Pat. Nos. 6,713,073; 6,592,869; 6,541,001; 6,509,446; 6,406,702; 6,319,693; 6,299,874; 6,286,455; 6,238,669; 6,048,535; 6,032,612; 5,958,424; 5,932,476; 5,884,583; 5,817,320; 5,750,111; 5,750,101; 5,561,062; 5,491,073; 5,422,109; 5,250,298; 5,149,530; 5,124,148; 5,118,502; 4,877,612; 4,795,635; 4,251,509; 4,235,876 and 3,949,070.

The method comprises administering to the animal an effective immunizing dose of the vaccine of the present invention. The effective immunizing dose following the stimulating acquisition of protective immunity by the peanut skin extract and/or the proanthocyanadin(s) may be optimized by routine experimentation known to one of ordinary skill in the art. The vaccine may be administered by any of the methods well known to those skilled in the art, for example, by intramuscular, subcutaneous (advantageously in neck skin), intraperitoneal, intravenous, orally, intradermal, intrabursal (just above the chickens vent), in ovo, or ocularly. Methods of administration are known to those skilled in the art. For example, U.S. Pat. Nos. 5,693,622; 5,589,466; 5,580,859; and 5,566,064 are hereby incorporated by reference in their entirety. Birds may also be administered vaccines in a spray cabinet. Birds may also be administered the vaccine in ovo, as described in U.S. Pat. Nos. 4,458,630 and 6,627,205, the disclosures of which are incorporated by reference.

Advantageously, birds are administered vaccines in a spray cabinet, i.e., a cabinet in which the birds are placed and exposed to a vapor containing vaccine, or by course spray. In another advantageous embodiment, the immunogenic or vaccine composition is administered orally. Alternatively, the immunogenic or vaccine composition can be administered in the drinking water or the feed, i.e., as a dietary supplement for about seven days.

Advantageously, the chicken is vaccinated at a young age. The chicken may be newly hatched or one day old when the vaccine is administered.

The invention encompasses a kit for preparing an immunogenic or vaccine composition which may comprise (i) the peanut skin extract described herein and/or any one or more of the proanthocyanadins described herein and/or any one or more of the vaccines described herein and (ii) a peanut skin extract, proanthocyanadin and/or a vaccine that is different from (i). The kit may comprise components (i) and (ii), in separate containers, optionally in the same package, and optionally with instructions for admixture and/or administration.

The invention also provides for a kit for performing the method any one of the methods described herein which may comprise (a) a peanut skin extract and/or one or more proanthocyanadins described herein and (b) a vaccine, in separate containers, optionally in the same package, and optionally with instructions for performing the method.

The invention will now be further described by way of the following non-limiting examples.

EXAMPLES

Example 1

Studies on immunostimulation using the coccidiosis model.

Experiments with PSE gave positive effects on the immune system and on protective immunity against coccidiosis, as measured by immune challenge after vaccination with live coccidia. PSE was extracted from raw peanut skins by boiling in distilled water, then dried by cryo-evaporation. The resulting residue was diluted with physiological saline to a wide range of concentrations (60-1000 mcg) and tested for toxicity to 18-day-old chicken embryos.

The inoculation of PSE seemed to have no toxic effects on the embryos, and did not appear to affect growth rate of the hatchling chicks. A laboratory strain of *Eimeria* tenella was used as live coccidiosis vaccine (1000 oocysts per bird), and was given by individual oral gavage to day-old chicks. At 28 days of age, each bird was challenged by inoculation of virulent cecal coccidia (a field isolate of *E. tenella* with a challenge dose of 100,000 oocysts per bird) or kept as unchallenged controls. Six days post-challenge, birds were euthanized for necropsy and lesion score (see, e.g., Johnson & Reid, 1970, Exper. Parasitol. 28:30-36). Weight gains were calculated. The vaccine used alone was only partially protective, as shown by a modest increase in weight gain and lower lesion scores, as compared with the unvaccinated control (Table 1). Partial protection is not uncommon with coccidiosis vaccines administered in this way in short term challenge experiments. Administration of PSE improved weight gain even at the lowest level (60 mcg). Higher levels of PSE gave better weight gains, and also an improvement in lesion scores. The best weight gains and lesion scores were at 250 mcg. These results demonstrated that over a range of 60-1000 micrograms of extract/embryo, the PSE was safe and effective as an immunomodulator for a coccidiosis vaccine.

TABLE 1

Effects of peanut skin extract given in ovo on development of protective immunity against *Eimeria tenella*. Broiler chicks challenged at 28 days of age with cecal coccidia (*E. tenella*). The letters refer to Duncan's Multiple Range (a post hoc test used to separate the means of groups).

| Trtmnt | Med | Immuniz | Challenge | Gain (g) 7 days Post-Challenge | Cecal Lesion Score[1] |
|---|---|---|---|---|---|
| 1 | No | No | No | 383 a | 0 e |
| 2 | No | No | Yes | 276 b | 3.04 a |
| 3 | No | Yes | Yes | 284 b | 2.22 b |
| 4 | P-60 | Yes | Yes | 358 a | 1.94 bcd |
| 5 | P-125 | Yes | Yes | 373 a | 2.21 b |
| 6 | P-250 | Yes | Yes | 381 a | 1.39 d |
| 7 | P-500 | Yes | Yes | 362 a | 1.78 bcd |
| 8 | P-1000 | Yes | Yes | 384 a | 2 bcd |

[1]Average of 60 birds/treatment (6 replicages of 10 birds each), scored on a scale of 0-4 where 0 = normal and 4 = severe.

The studies comprised of a large, well-controlled experiment, which demonstrates that the constituents of PSE are useful stimulators of immunity to poultry coccidiosis when injected into the developing embryo at 18 days. Application of PSE in this way had no apparent deleterious effects.

TABLE 2

Effects of peanut skin extract and/or vitamin E (in IU) given in ovo on development of protective immunity against *Eimeria tenella*. Broiler chicks challenged at 28 days of age with cecal coccidia (*E. tenella*). The letters refer to Duncan's Multiple Range (a post hoc test used to separate the means of groups)

| Group | Mean Gain N | Duncan's | Mean Cecal Score N | Duncan's |
|---|---|---|---|---|
| Peanut 500 ug | 321 | 77 c | 0.97 | 77 cd |
| Peanut 100 ug | 314 | 86 c | 0.74 | 86 d |
| Peanut 50 ug | 312 | 74 c | 1.58 | 74 b |
| Unimm/Inf | 287 | 50 d | 2.3 | 50 a |
| Unimm/Uninf | 381 | 48 a | 0 | 48 e |
| Imm/Inf | 351 | 60 b | 1.33 | 60 cb |
| E10 | 361 | 52 a | 1.53 | 52 cd |
| E20 | 357 | 53 a | 1.73 | 53 cbd |
| E30 | 388 | 43 a | 1.55 | 43 cd |
| Peanut 100 ug | 383 | 48 a | 2 | 48 cb |
| Peanut 500 ug | 361 | 54 a | 1.77 | 54 cbd |
| Peanut 250 ug | 381 | 52 a | 1.38 | 52 d |
| Peanut 125 ug | 372 | 53 a | 2.2 | 53 b |
| Peanut 60 ug | 358 | 53 a | 1.94 | 53 cbd |
| Unimm/Inf | 275 | 50 b | 3.04 | 50 a |
| Unimm/Uninf | 382 | 51 a | 0 | 51 e |
| Imm/Inf | 283 | 58 b | 2.22 | 58 b |
| E10 | 438 | 43 a | 1.46 | 43 b |
| E10/P100 | 409 | 38 bac | 0.21 | 38 ef |
| E10/P500 | 349 | 42 fdec | 0.47 | 42 efd |
| E10/P125 | 330 | 38 fe | 1.42 | 38 b |
| E20 | 322 | 14 fe | 1.21 | 14 cbd |
| E20/P100 | 321 | 22 fe | 1.09 | 22 cbd |
| E20/P500 | 354 | 22 fdec | 2.31 | 22 a |
| E20/P125 | 330 | 38 fe | 1.44 | 9 b |
| E30 | 454 | 16 a | 0.5 | 16 efd |
| E30/P100 | 345 | 27 fde | 1.33 | 27 cb |
| E30/P500 | 363 | 17 fbedc | 1.16 | 18 cbd |
| E30/P125 | 360 | 19 fbedc | 0.57 | 19 cefd |
| Peanut 1000 | 342 | 49 fde | 1.18 | 49 cbd |
| Peanut 500 | 400 | 46 bdac | 0.95 | 46 cebd |
| Peanut 125 | 378 | 56 bdec | 0.64 | 56 cefd |
| Unimm/Inf | 306 | 90 f | 2.26 | 90 a |
| Unimm/Uninf | 415 | 87 ba | 0 | 87 f |
| Imm/Inf | 355 | 89 fdec | 1.47 | 89 b |

Example 2

Identification of the optimal dosage of active ingredients in peanut skin extract (PSE) for immunostimulation in combination with five coccidiosis vaccines, and demonstration of the safety of PSE for broiler chickens.

The model for test of effectiveness in combination with a live coccidiosis vaccine is described in Example 1 and as follows. Embryos are inoculated at 18 days of incubation with graded doses of PSE or purified proanthocyanidin. The procedure for inoculation in ovo is similar to that used in commercial practice, with the Embrex technique (see, e.g., Ricks, et al, 1999, 1999. In ovo vaccination technology. Adv. Vet. Med. 41:495-515. Academic Press, San Diego Calif.), or the Inovoject process, both of which are widely practiced in the USA and South America. Controls are inoculated with an equivalent volume of physiological saline. Coccidiosis live vaccine is given after hatch (day-old) by the spray-cabinet technique, similar to a commercial procedure widely used in the poultry industry. The chicks thus treated are transferred to battery cages or to floor pens with fresh litter and unmedicated feed and water. At 28 days of age, groups of birds are selected from each pen/cage for challenge. Birds are weighed and distributed to cages randomly within treatment, with adequate replication for statistical comparisons (4-6 replicates of 10 birds/cage). Birds are challenged by individual gavage of a dose of sporulated oocysts which would be expected to produce severe lesions and reduced weight gain in immunologically naive birds. Each challenge test also contains unchallenged birds from each of the embryo-treatments, as well as separately-reared unexposed birds to serve as naive controls. The test is terminated after 6-7 days. Weight gains are determined, then birds are euthanized for necropsy. Each bird is examined for lesions of the species of coccidia used in the challenge, in the intestinal tract, and recorded on a scale of 0-4, where 0=normal and 4=most severe (see, e.g., Johnson & Reid, 1970, Exper. Parasitol. 28:30-36).

There are several important species of coccidia in chickens, and it is well known that each stimulates the development of immunity separately from the others (see, e.g., McDougald, 2003, Coccidiosis. In Diseases of Poultry, 11" edition, ed by Y. M. Saif, H. J. Barnes, J. R. Glisson, A. M. Fadly, L. R McDougald, and D. E. Swayne. Iowa State Press, Ames Iowa, pp. 974-990). There is no cross-immunity between species resulting from natural infections. Thus, it is necessary to repeat the experiments described above for those species deemed important, or at least those included in coccidiosis vaccines. The experiments described in Example 1 utilized *Eimeria tenella*, known as canal coccidiosis. Other species to be tested would include *E. acervulina, E. maxima,* and *E. mitts*. Test of each of these species is essentially similar, except for the location and appearance of lesions in the intestine. Cultures of each of the species needed for these studies are maintained frozen in liquid nitrogen, and in ready culture by routine reinfection and collection from chickens. There are no culture techniques for production of infective coccidia in vitro, requiring that all testing be done in live animals, by challenge infection.

Medicinal articles are often mixed with the feed to be given to chickens for short or long periods, as an alternative to other means of administration. Some immunostimulants were effective when administered in this way. An experiment with design similar to that shown in the study of Example 1 is conducted with the PSE given as a dietary supplement for the first week of feeding. Hatchling chicks given no prior injections are vaccinated at day-old with the live coccidiosis vaccine and given PSE in a complete feed for 7 days while housed in battery cages. Three levels of PSE are chosen from prior studies for this study. Birds are challenged at 28 days of age, as described in the study of Example 1, with virulent reference strains of the coccidia contained in the vaccine. Treatments include uninoculated and unvaccinated; inoculated and unvaccinated (for each level of PSE); vaccinated and uninoculated; inoculated and vaccinated (for each level of PSE). Unchallenged controls are maintained as weight gain controls. Protective immunity is determined by comparison of the weight gains post challenge and the lesion scores at necropsy, with other birds not given PSE. The experiment consists of 6 replicates of each treatment, with 10 birds/cage for a total of 60 birds for each treatment.

Birds can be vaccinated or medicated in the hatchery by subcutaneous inoculation (SC) in the neck skin. This is potentially a route for administration of PSE. An experiment is conducted similar to that described in the study of Example 1 and as described above. Newly-hatched chicks with no prior vaccinations are divided randomly into groups for inoculation SC, or kept as controls. The level of PSE to be injected per bird is determined as an optimal dose from prior studies, as well as a higher level. These chicks are further divided into two treatments of vaccinated or unvaccinated. A live coccidiosis vaccine is given by spray cabinet, according to commercial practices. The chicks are grown to 28 days of age and challenged with reference coccidia as described above. A comparison is made between challenged and unchallenged birds for assessment of treatments on weight gain and lesion scores, as described above.

The effects of PSE on growth, feed efficiency, hatchability of injected eggs, and mortality are determined. Essential to the use of any product in broiler chickens is its lack of adverse effects on economically important production parameters. The following experiment is repeated in at least three trials, using a commercial strain of broilers, grown to market weight. Embryos are injected at 18 days with orange of doses of PSE (3 levels) or physiological saline. The number of chicks hatched at the normal time of 20-22 days is recorded. Chicks from each injection treatment are randomly distributed in clean floor pens with fresh litter. No vaccines are given. The birds are reared to market weight in approximately 42 days. Feed consumption is recorded. The number of birds and weight of each pen of birds is recorded at each change of feed (19 and 35 days) and at the end. Mortality is recorded daily. Feed conversion is calculated for each feeding period. Each treatment is replicated in 8 pens of 40 birds, for statistical analysis.

Example 3

Use of appropriate disease models to identify other vaccines in poultry where significant responses to PSE could enhance effectiveness of the vaccine and promote increased productivity and protective responses.

Of particular importance is determination of the effects of PSE on response of chickens to viral and bacterial diseases. Live vaccines are used for several viral diseases, such as, but not limited to, Muck's disease, Newcastle disease, infectious bursal disease, laryngotracheitis, and infectious bronchitis. To establish antiviral immunostimulation, PSE is initially tested in concert with live vaccines for Newcastle disease and infectious bronchitis. Each of these tests is set up in the same way, with embryos injected with PSE at 18 days of development. Hatchling chicks is vaccinated with Newcastle vaccine (common type used in USA for broilers) at day-old, or kept as unvaccinated controls. Chicks are housed in isolators with filtered air to preclude extraneous infection with wild or vaccine viruses. Blood is drawn at 28 days of age and tested for antibody titers, using standard procedures. Procedures for titering blood sera from poultry are standard and routine. Other birds are challenged with virulent Newcastle or infectious bronchitis virus to measure the protective immunity. Because these studies involve contagious organisms, they are conducted in isolators. Stimulated or unstimulated birds are vaccinated with a live Newcastle or infectious bronchitis vaccine and placed in Steam sterilized isolators. At 28 days of age, the birds are challenged with a virulent strain of Newcastle disease or infectious bronchitis virus. The degree of protection from the vaccine is measured by weight gain, mortality, and respiratory signs.

Example 4

Determination of the effects of PSE on immune function by measuring effects on lymphokines, T-cell subsets, lymphocyte transformation, antibody production, and other aspects of the immune response.

Characterization of the effects of PSE on immune function is important to demonstrate the nature of the response of the bird and to prove that the improvements in apparent protection are due to immune function and not a result of other reactions. Further, this characterization guides the optimization of the route and dose of application of PSE. These tests are standard for study of immune function in mammals and birds.

Macrophages are obtained by interperitoneal injection of birds with a 3% suspension of sephadex-G50 (1 ml/100 g body wt). Abdominal exudates are harvested 42 hours later by flushing the abdominal cavity with 30 ml of Dulbecco's vbalanced salt solution with gentimicin and heparin (0.5 µl). Macrophages are pelleted by centrifugation and resuspended in RPMI 1640, 3% fetal bovine serum gentimicin to be used for proliferative effects, phagocytic potential, FC mediated rosette assay, or quantification of nitrate production.

Naive 4 week old unstimulated birds are used to obtain macrophages to determine the proliferative effects of PSE. Macrophage proliferation is determined as previously described (see, e.g., Guo et al., 2003, Immunopharm. Immunotoxicol 25, pp 461-472) with the exception that the WST-8 assay is used for cell proliferation (see, e.g., Miyamoto et. al., 2002, Avian Dis. 46, pp. 10-16). Macrophages ($5 \times 10^4$ cell/100 µl complete RPMI 1640) are added to 96 well tissue culture plates and incubated for 30 minutes at 41 C. Controls consist of medium without PSE or with serial dilutions of PSE added to wells to a final volume of 200 µl. Each preparation is replicated in 4 wells/plate and in duplicate plates. Macrophages are incubated for 24 hours at 41 C and 5% humidity, then 10 µl of supernatant removed and 10 µl of WST-8 solution added. The plates are incubated for 1-4 hours and then absorbance at 450 nm read using a microplate reader. Proliferation due to PSE is expressed as percentage of growth in stimulated cells relative to control.

The macrophage phagocytic potential is determined as follows. Macrophages are collected from 4 week old naive/unstimulated birds. Macrophages ($1 \times 10^6$ cell/100 µl complete RPMI 1640) are added to 96 well tissue culture plates. Negative controls consist of medium without PSE and with serial dilution of PSE added to wells to a final volume of 100 µl. Each test is replicated in 4 wells and in duplicate plates. Cells are incubated for 1 hour (41 C 5% $CO_2$) to allow for adherence of macrophages. After incubation medium is removed by aspiration, 100 µl of fluorescent bioparticle suspension (Molecular Probes, Vybrant Phagocytosis Assay) is added to all wells. Plates are then incubated for 2 hours (41 C 5% $CO_2$). Microplates are read in a fluorescence plate reader using 480 nm excitation, 520 nm emmission. Phagocytic response is expressed as % effect as a ratio of experimental reading (PSE) to positive reading (normal phagocytosis) (see, e.g., Wan, et. al. 1993, J. Immunol. Methods 162, pp. 1-7).

Macrophage nitrite production is determined as follows. Macrophages are collected from 4 week old naive/unstimulated birds. Macrophages ($1 \times 10^6$ cell/100 µl complete RPMI 1640) are added to 24 well tissue culture plates. Negative controls consist of medium without PSE and serial dilution of PSE added to a final volume of 100 µl/well. All levels are replicated in 4 wells and in duplicate plates. Cells are then incubated for 24 hours in the presence of PSE (41 C, 5% $CO_2$). After incubation, culture supernatant fractions are removed and assayed for nitrite production using the Greiss method (see, e.g., Green et al., 1982, Anal. Biochem. 126: 131-138).

Lymphocye proliferation is measured as follows. Whole blood is used as a source for PBL. Blood is collected from PSE stimulated, vaccinated birds and controls at 7, 14, and day 21 post vaccination. Blood is collected via cardiac puncture in heparinized syringes, and then diluted with Dulbecco's Balanced Salt Solution. Spleens from PSE stimulated, vaccinated birds and controls are aseptically collected at 7, 14, and day 21 post-vaccination and macerated through stainless steel screens to obtain single cell suspensions. Blood and cell suspensions are overlaid onto HISTOPAQUE 1077 density gradient and centrifuged at 400 g for 30 minutes at room temperature. Lymphocytes at the opaque interface are removed and washed by centrifugation at 200 g for 10 minutes×3. Viable cells are counted using FDA/propidium iodide uptake. Cells are plated at $2.5 \times 10^6$ cells/well in 96 well flat bottomed plates. Complete medium consists of RPMI 1640 (L-glutamine, 100 U penicillin/ml, 100 µg streptomycin/ml, $2 \times 10^6$ M 2-mercaptoethanol, 5 µg 5-flurocytosine/ml, and 1 mM sodium pyruvate). Cells are stimulated by the addition of Con A (5 µg/well). Unstimulated wells are used as controls. All assays are performed in replicates of 4 on duplicate plates. Plates are incubated for 48 hours in 5%. $CO_2$ 95% humidity, at which time 10 µA of WST-8 is added. Plates are incubated for 4 hours and the OD of each well measured at 450 nm with a microtiter plate reader. The stimulation index is calculated as SI=mean OD of Con A stimulated cells/mean OD of unstimulated cells (see, e.g., Miyamoto et al., 2002, Avian Dis. 46, pp. 10-16).

Bioassays for IFN-γ are conducted according to Kaspers et al. (1994, Vet. Immun. Immunopath. 44:71-84) and Martin et al. (1995, Avian Dis. 39:538-547). Interferon secretion is induced by culturing splenic lymphocytes from chickens in all treatment groups. Chicken embryo fibroblasts are pretreated for 12-18 hrs with culture supernatants from mitogen activated splenocytes as an IFN-γ source, then infested for 48 hrs with vesicular stomatitis virus and cytotoxicity levels determined. Titers are determined by the highest dilution of supernatant showing protection against virus killing.

Example 5

Determination of the optimum methods for extraction and concentration of the active ingredients of PSE.

While the extraction of active PSE from raw material is easily accomplished by the boiling water method, quantitative studies have not been done. To study this procedure, PSE is extracted from peanut skins in boiling water, as described by Lou et al. (1999, Phytochem. 51:297-308). The extract is concentrated by cryo-evaporation to dryness and reconstituted in physiological saline for injection. The yield of PSE is determined using several batches of raw material from diverse sources. The concentration of proanthocyanidins in PSE, and the relative concentrations of each of the major proanthocyanidin compounds in the extracts is characterized by the HPLC methods of Lou et al. (1999, Phytochem. 51:297-308). Quantitative purification of the major fractions is developed by column chromatography, to provide material for other studies. An assay for proanthocyanidins is developed, based on the HPLC method of Lou et al. (1999, Phytochem. 51:297-308) so that the dosages used in biological studies can be accurately determined.

Example 6

Identification of the pro-anthocyanadins in PSE and determination of the relative activity of major components.

Individual compounds in PSE are selected for biological testing, on the basis of their relative concentration in the extract. According to the work of Lou et al. (1999, Phytochem. 51:297-308), peanut skins contain six proanthocyanidins. Five proanthocyanadins were isolated and identified as epicatechin-(2β→O→7, 4β→6)-[epicatechin-(4β→8)]-catechin (1), epicatechin-(2β→O→7, 4β→8) epicatechin-(4β→8)-catechin-(4α→8)-epicatechin (2) and procyanidins B2 (3), B3 (4) and B4 (5) (see, e.g., Lou et al., Phytochemistry, 2004 August; 65(16):2391-9). Each selected compound is tested in the coccidiosis live vaccine model described in Examples 1 and 2. These tests are both quantitative and qualitative. First, each of the compounds is tested in a range of doses, in the manner described in Example 1 using the coccidiosis live vaccine model. The apparent optimum level of each of these compounds are compared in a subsequent test involving all of the purified compounds.

Additionally, each compound would be tested for safety, as described in Example 2. Embryos 18 days old are injected with graded doses of the test substance (3 levels), or with physiological saline. After hatch, chicks are transferred to cages and grown for 28 days, for measurement of growth, feed consumption, and mortality. Each treatment is replicated in 8 cages of 10 birds each, to allow statistical analysis.

Example 7

Economic analysis to determine the value of PSE in relation to current uses for peanut skins.

The current value of peanut skin raw material is based on its use as a livestock feed. The analysis takes into account the tonnage of raw material available, the amount of proanthocyanidins which can be extracted (PSE), and the value of the PSE for the proposed use. Further, a cost/benefit analysis is conducted on the intended application in the broiler industry, to determine economic feasibility and potential selling price of a proposed product.

The invention is further described by the following numbered paragraphs:

1. An immunogenic or vaccine composition comprising a vaccine and an adjuvant comprising a peanut skin extract.
2. The composition of paragraph 1 wherein the composition further comprises a pharmaceutically effective carrier.
3. The composition of paragraph 1 or 2 wherein the vaccine is a coccidiosis vaccine.
4. The composition of paragraph 3 wherein the coccidiosis vaccine comprises one of more strains of *E. acervulina, E. maxima, E. mitis* or *E. tenella*.
5. The composition of paragraph 4 wherein the cocciodiosis vaccine comprises *E. tenella*.
6. The composition of paragraph 1 or 2 wherein the vaccine is a infectious bronchitis vaccine, infectious bursal disease vaccine, laryngotracheitis vaccine, Marek's disease vaccine or Newcastle disease vaccine.
7. The composition of paragraph 6 wherein the vaccine is an infectious bronchitis vaccine or Newcastle disease vaccine.
8. An immunogenic or vaccine composition comprising a vaccine and an adjuvant comprising one or more proanthocyanadins.
9. The composition of paragraph 8 wherein the composition further comprises a pharmaceutically effective carrier.
10. The composition of paragraph 9 wherein the proanthocyanadin is selected from the group consisting of epicatechin-(2β→O→7, 4β→6)-[epicatechin-(4β→8)]-catechin, epicatechin-(2β→O→7, 4β→8) epicatechin-(4β→8)-catechin-(4α→8)-epicatechin, procyanidin B2, procyanadin B3 and procyanadin B4.
11. The composition of any one of paragraphs 8 to 10 wherein the vaccine is a coccidiosis vaccine.
12. The composition of paragraph 11 wherein the coccidiosis vaccine comprises one of more strains of *E. acervulina, E. maxima, E. mitis* or *E. tenella*.
13. The composition of paragraph 12 wherein the cocciodiosis vaccine comprises *E. tenella*.
14. The composition of any one of paragraphs 8 to 10 wherein the vaccine is an infectious bronchitis vaccine, infectious bursal disease vaccine, laryngotracheitis vaccine, Marek's disease vaccine or Newcastle disease vaccine.
15. The composition of paragraph 14 wherein the vaccine is an infectious bronchitis vaccine or Newcastle disease vaccine.
16. The composition of any one of paragraphs 1 to 15 wherein the vaccine is a live vaccine.
17. A method for eliciting an immune response comprising administering an effective amount of the immunogenic or vaccine composition of any one of paragraphs 1 to 16 to induce the response in a chicken.
18. A method for inducing an immunological or protective response comprising administering an effective amount of the immunogenic or vaccine composition of any one of paragraphs 1 to 16 to induce the response in a chicken.
19. The method of paragraph 17 or 18 wherein the immunogenic or vaccine composition is administered to a chicken by oral gavage.
20. The method of paragraph 17 or 18 wherein the immunogenic or vaccine composition is administered to a chicken in a spray cabinet.
21. The method of paragraph 17 or 18 wherein the immunogenic or vaccine composition is administered to a chicken as a dietary supplement.
22. The method of paragraph 17 or 18 wherein the immunogenic or vaccine composition is administered to a chicken as a subcutaneous injection.
23. The method of paragraph 22 wherein the administration is in neck skin.
24. The method of any one of paragraphs 16 to 23 wherein the chicken is newly hatched.
25. The method of any one of paragraphs 16 to 23 wherein the chicken is one day old.
26. A method of stimulating acquisition of protective immunity comprising administering an effective amount of peanut skin extract prior to vaccination with an effective amount of a vaccine to stimulate acquisition of protective immunity in a chicken.

27. The method of paragraph 26 wherein the amount of peanut skin extract is about 60 micrograms to about 1000 micrograms.

28. The method of paragraph 27 wherein the amount of peanut skin extract is about 250 micrograms.

29. A method of stimulating acquisition of protective immunity comprising administering an effective amount of one or more proanthocyanadins prior to vaccination with an effective amount of a vaccine to stimulate acquisition of protective immunity in a chicken.

30. The method of paragraph 29 wherein the proanthocyanadin is selected from the group consisting of epicatechin-(2β→O→7, 4β→6)-[epicatechin-(4β→8)]-catechin, epicatechin-(2β→O→7, 4β→8) epicatechin-(4β→8)-catechin-(4α→8)-epicatechin, procyanidin B2, procyanadin B3 and procyanadin B4.

31. The method of any one of paragraphs 26 to 30 wherein the chicken is a chicken embryo.

32. The method of paragraph 31 wherein the chicken embryo is an 18 day chicken embryo.

33. The method of any one of paragraphs 25 to 32 wherein the administration of the effective amount of peanut skin extract or effective amount of one or more proanthocyanadins is by injection.

34. The method of any one of paragraphs 25 to 32 wherein the vaccination with the effective amount of a vaccine is administered to a chicken by oral gavage.

35. The method of any one of paragraphs 25 to 32 wherein the immunogenic or vaccine composition is administered to a chicken in a spray cabinet.

36. The method of any one of paragraphs 25 to 32 wherein the immunogenic or vaccine composition is administered to a chicken as a dietary supplement.

37. The method of any one of paragraphs 25 to 32 wherein the immunogenic or vaccine composition is administered to a chicken as a subcutaneous injection.

38. The method of any one of paragraphs 25 to 32 wherein the administration is in neck skin.

39. The method of any one of paragraphs 25 to 38 wherein the chicken is newly hatched.

40. The method of any one of paragraphs 25 to 38 wherein the chicken is one day old.

41. An immunogenic or vaccine composition comprising (i) the peanut skin extract from the compositions of paragraphs 1 to 7 and 16 or the methods of paragraphs 17 to 28 and 31 to 40 to 43, and/or the proanthocyanadin from the compositions of paragraphs 8 to 16 or the methods of paragraphs 17 to 25 and 29 to 40 and/or the vaccine from the compositions of paragraphs 1 to 16 or the methods of paragraphs 17 to 40 and/or (ii) a peanut skin extract, proanthocyanadin and/or a vaccine that is different from (i).

42. A kit for preparing the immunogenic or vaccine composition of paragraph 41 comprising (a) component (i) and (b) component (ii), in separate containers, optionally in the same package, and optionally with instructions for admixture and/or administration.

43. A kit for performing the method of any one of paragraphs 17 to 40 comprising (a) a peanut skin extract and/or a proanthocyanadin and (b) a vaccine, in separate containers, optionally in the same package, and optionally with instructions for performing the method.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A protective immunogenic or vaccine composition, which is effective against coccidiosis in a chicken comprising:
    (a) at least one parasite, microorganism, antigen, immunogen, epitope or vaccine; and
    (b) an adjuvant consisting essentially of:
        (i) 60 to 1000 micrograms of a peanut skin extract (PSE), which extract has been prepared via boiling water extraction, followed by concentration by cryo-evaporation, and
        (ii) optionally 10 to 30 IU of vitamin E; and
    wherein chicks that had been previously in ovo inoculated with the PSE-adjuvanted vaccine gain at least 20% more weight, 7 days post-challenge with cecal coccidia, relative to chicks previously in ovo inoculated with the same vaccine where the PSE has been omitted; and
    an appropriate pharmaceutical or veterinary carrier or vehicle.

2. The composition of claim 1 wherein the effective amount of peanut skin extract is about 250 micrograms.

3. The composition of 1 which is formulated to be administered to a chicken embryo; and wherein the chicken embryo is an 18 day chicken embryo.

4. The composition of claim 3 which is formulated to be administered by in ovo injection.

5. A method of eliciting an immune response in a chicken comprising administering in ovo to the chicken an effective amount of a vaccine according to claim 1.

6. The method of claim 5 wherein the coccidiosis vaccine comprises one or more strains of *E. acervuline, E. maxima,* or *E. tenella.*

7. A kit for use in stimulating acquisition of protective immunity against coccidiosis in a chicken, wherein said kit comprises (a) a peanut skin extract and (b) at least one strain of coccidia, in separate containers, optionally in the same package, and optionally with instructions for performing the method.

* * * * *